(12) United States Patent
Black et al.

(10) Patent No.: US 11,585,807 B2
(45) Date of Patent: Feb. 21, 2023

(54) NANOTEXTURED SILICON BIOSENSORS (71) Applicant: Advanced Silicon Group, Inc., Lincoln, MA (US)

(72) Inventors: Marcie R. Black, Lincoln, MA (US); Edward Van Corbach, Groton, MA (US); William Rever, Linthicum Heights, MD (US)

(73) Assignee: Advanced Silicon Group, Inc., Lincoln, MA (US)

( * ) Notice: Subject to any disclaimer, the term of this patent is extended or adjusted under 35 U.S.C. 154(b) by 0 days.

(21) Appl. No.: 16/793,280

(22) Filed: Feb. 18, 2020

(65) Prior Publication Data

US 2020/0264118 A1   Aug. 20, 2020

Related U.S. Application Data

(60) Provisional application No. 62/808,259, filed on Feb. 20, 2019.

(51) Int. Cl.
*G01N 33/543* (2006.01)
*G01N 27/12* (2006.01)
*H01L 31/0352* (2006.01)
*B82Y 15/00* (2011.01)

(52) U.S. Cl.
CPC ........ *G01N 33/54306* (2013.01); *B82Y 15/00* (2013.01); *G01N 27/127* (2013.01); *H01L 31/035227* (2013.01)

(58) Field of Classification Search
CPC .......... G01N 33/54306; G01N 27/127; B82Y 15/00; H01L 31/035227
See application file for complete search history.

(56) References Cited

U.S. PATENT DOCUMENTS

| | | | |
|---|---|---|---|
| 8,143,143 B2 | 3/2012 | Buchine et al. | |
| 8,450,599 B2 | 5/2013 | Buchine et al. | |
| 8,852,981 B2 | 10/2014 | Black et al. | |
| 10,079,322 B2 | 9/2018 | Black et al. | |
| 2009/0256134 A1 | 10/2009 | Buchine et al. | |
| 2012/0153250 A1* | 6/2012 | Modawar | H01L 31/028 438/57 |
| 2017/0052182 A1 | 2/2017 | Black et al. | |

OTHER PUBLICATIONS

Galinski et al., "Agglomeration of Pt thin films on dielectric substrates," Phys. Rev. B, 82, 235415 (2010).
Liu et al., "Efficient SERS substrates made by electroless silver deposition into patterned silicon structures," J. Mater. Chem., 14, 1526-1532 (2004).
Pashley et al., "The growth and structure of gold and silver deposits formed by evaporation inside an electron microscope," Phil. Mag., 10:103, 127-158 (1964).

(Continued)

*Primary Examiner* — Melanie Brown
(74) *Attorney, Agent, or Firm* — Lando & Anastasi, LLP (57) ABSTRACT

Provided is a sensor with nanowires in an aligned array. In one example, the heaviest doped region is not in the nanowire array, but in the bulk silicon substrate and the sensor is functionalized to be have modified electrical properties when proteins are present.

12 Claims, 5 Drawing Sheets

(56) References Cited

OTHER PUBLICATIONS

Smith et al., "Surface Modifying Doped Silicon Nanowire Based Solar Cells for Applications in Biosensing", Advanced Materials Technologies, 1800349 (2018).
Zheng et al., "Multiplexed electrical detection of cancer markers with nanowire sensor arrays", Nature Biotechnology, vol. 23, No. 10, Oct. 2005, pp. 1294-1301.
Franssila, "Introduction to Microfabrication," 2d. ed., John Wiley & Sons, 2010.
Muller et al., "Device electronics for integrated circuits." (1986).
Weste et al., "Principles of VLSI Design." A Systems Perspective 2 (1985).

* cited by examiner

NANOTEXTURED SILICON BIOSENSORS

CROSS-REFERENCE TO RELATED APPLICATIONS

This Application is related to and claims priority to U.S. Provisional Application No. 62/808,259, entitled "NANOTEXTURED SILICON BIOSENSORS" (BLACK, Marcie R. et al.) filed on Feb. 20, 2019.

BACKGROUND OF THE INVENTION

Millions of people are diagnosed with cancer, or related illness, each year. Unfortunately for many of the diagnosed, the survival rates are not high. Accordingly, billions of dollars in resources and capital are being expended each year to care for and provide health care services to those diagnosed with cancer related illnesses. In particular, the Agency for Healthcare Research and Quality (AHRQ) estimated that the sum of all health care costs for cancer in the United States in 2011 was approximately $88.7 billion.

Often, targeted therapy can be useful in targeting particular types of cancer. Targeted therapy typically includes application of specialized drugs to fight the responsive type of cancer. Targeted therapies are typically useful when a corresponding mutation is identified, and tend to provide better efficacy with less side effects when compared to generic cancer treatments.

Early detection can also lower the cost of treatment, and can increase the survival chances of a diagnosed patient. According to some estimates, treating a patient for cancer can average around a million dollars per patient. Various costs can be distributed among costs associated with hospital outpatient or doctor office visits, inpatient hospital stays, and prescription drugs, with the majority of expenses being associated with the outpatient or doctor office visits.

While various early detection methods do exist, existing approaches have inconsistent levels of accuracy and efficacy. In particular, conventional cancer detection approaches are generally not suitable for early detection. Currently, cancer is first detected by physical examination in combination with imaging studies, such as CT scans or MRIs. Routine blood tests may also reflect organ dysfunction, or other symptoms which are caused by cancer. However, such approaches generally are most effective after the cancer has significantly damaged the patient, at which point it may be too late for treatment. Moreover, existing approaches are unable to detect all types of cancer cells.

Accordingly, a low-cost early detection method for cancer is not only critical to relieve the economic burdens on the healthcare system, but to also save lives.

Nanowire arrays are seeing increasing use in a variety of applications. See, e.g., U.S. Published Patent Application No. 2009/256134 titled "PROCESS FOR FABRICATING NANOWIRE ARRAYS" offers one such example of a nanowire array, and is incorporated by reference herein in its entirety. A typical nanowire array might consist of a collection of silicon nanowires, on the order of 100-200 nm in diameter, and on the order of about a hundred nm to hundreds mm in height. Each nanowire may have an approximately cylindrical or frustoconical shape. In contrast to typical nanowire arrays which arrange each individual nanowire in a horizontal orientation relative to associated base surface, various examples of the nanowires discussed herein have an axis which may run approximately parallel to each other and in a vertical direction relative to the base surface (e.g., the substrate to which the nanowires are mounted). Accordingly, each nanowire may be attached at an end to the silicon substrate.

A silicon nanowire array on top of a silicon substrate can alter the opto-electrical properties of the bulk silicon substrate. For example, a silicon nanowire array may reduce the reflection of the silicon substrate, reduce the reflection at off-angles of incidence, and increase the absorption of the silicon in ways similar to traditional pyramids or light trapping mechanisms used in solar cells.

Nanowires can also be used to make biosensors. A nanowire can have a high surface area to volume ratio, and therefore has the characteristics to make a very sensitive detector. Each individual nanowire of the nanowire array may be defined by a longitudinal surface and a vertical surface. In certain examples, the longitudinal surface of each nanowire is at least two times longer than the vertical surface. Accordingly, the vertical arrangement of the nanowire allows the nanowire to have a significantly increased density of individual nanowires (e.g., at least 1000 nanowires per $cm^2$) when compared to typical horizontal arrangements. Such an arrangement significantly improves the sensitivity of the biosensor.

Figure 1:
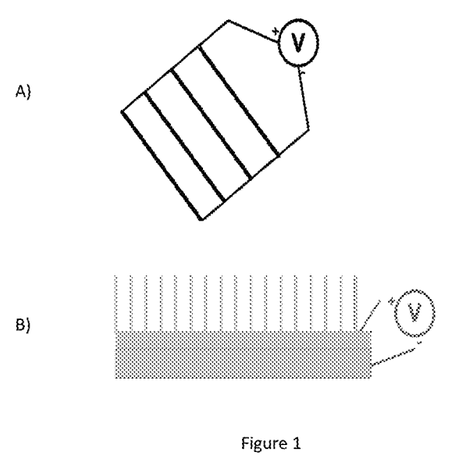

Provisional US patent application US20170052182A1 teaches using vertically aligned silicon nanowire arrays for the detection of protein and DNA concentrations. This patent application differs from previous approaches to nanowire biomarker detection which only measure electrical measurements, such as conductance probing. For example, in one such approach distinct nanowires and surface receptors are incorporated into horizontal nanowire field-effect-transistor arrays. One challenge is that electrical detection for horizontal wires requires that each of the nanowires is electrically contacted on both sides. This requirement makes using many nanowires challenging at least because of the complex device fabrication steps to contact the wires. The vertically aligned nanowires taught in US20170052182A1 solves this contacting challenge. See FIG. 1 A) for horizontally aligned nanowires which need an electrical contact at both ends of the nanowires and FIG. 1 B) for vertically aligned nanowires. Thus, vertically aligned nanowires are much easier to scale and manufacture since the manufacturer is not required to electrically contact each individual nanowire. Instead, one can look at the effect of the change in the electrical properties of the nanowires when exposed to biomarkers on the underlying test chip, thus allowing many more nanowires to be measured.

Figure 2:
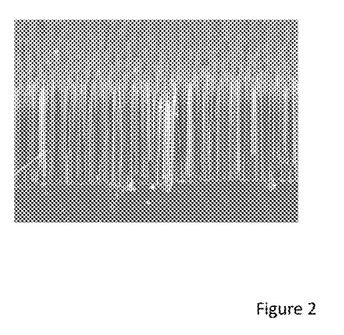
FIG. 2: a cross-sectional scanning electronic microscope image of nanowires arrays made with metal-enhanced etching.

A common method for making silicon nanowires is metal-enhanced etching of a silicon-containing substrate. See FIG. 2 for a cross sectional scanning electronic microscope image of nanowires arrays made with metal-enhanced etching. This process can be used to control the nanowire dimensions and is described in U.S. Pat. No. 8,143,143, titled "PROCESS FOR FABRICATING NANOWIRE ARRAYS", and U.S. Pat. No. 8,450,599, titled "NANOSTRUCTURED DEVICES", which are both incorporated by reference in their entirety. In metal-enhanced etching, a metal is deposited on top of a silicon substrate and placed in a solution in which the etch is enhanced wherever the silicon touches metal. Since the metal coverage is not uniform, parts of the silicon are not etched leaving a graded index silicon, cliffs, or nanowires. The metal used can be, for example, gold, platinum, or silver.

Other typical techniques for forming silicon nanowires may include reactive ion etching and VLS (Vapor-Liquid- Solid). During VLS processes, nanowires are grown on a substrate using a metal catalyst and silane.

SUMMARY OF THE INVENTION

In an embodiment of the disclosure, a silicon nanowire biosensor is described with multiple subsensors to measure different analytes.

BRIEF DESCRIPTION OF THE FIGURES

FIG. 1: A) a schematic of horizontally aligned nanowires which need an electrical contact at both ends of the nanowires and FIG. 1 B) vertically aligned nanowires which are easier to electrically contact.

DETAILED DESCRIPTION OF THE INVENTION

Before describing the present invention in detail, it is to be understood that this invention is not limited to specific solvents, materials, or device structures, as such may vary. It is also to be understood that the terminology used herein is for the purpose of describing particular embodiments only, and is not intended to be limiting.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also disclosed, as well as the range of values greater than or equal to 1 µm and the range of values less than or equal to 8 µm.

Examples of the systems and methods discussed herein are not limited in application to the details of construction and the arrangement of components set forth in the following description or illustrated in the accompanying drawings. The systems and methods are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated features is supplementary to that of this document; for irreconcilable differences, the term usage in this document controls.

Aspects and embodiments are generally directed to sensors (e.g., biosensors) including large arrays of nanowires and some aspects of the invention include improvements to the biosensor disclosed in patent application US20170052182A1. An array of nanowires may be formed on a test chip. The sensor of various embodiments may be constructed by fabricating at least one nanowire array, forming a solar cell by doping the top surface of a substrate, electrically contacting the substrate to the nanowire array, and functionalizing (e.g., chemically coating) the nanowires. The nanowires can be incorporated onto a test chip which may be exposed to a sample to determine the presence, absence, or concentration of an analyte within the sample.

As discussed herein, functionalization may refer to coating a nanowire with a desired chemical which is sensitive to an analyte (e.g., a biomarker binding agent) or protein. In many cases this functionalization results in attaching an antibody or aptamer to the silicon surface. The antibody or aptamer selectively binds to other organic material such as a protein. When the functionalized nanowires are exposed to the protein or analyte for which they are functionalized for, their electrical properties may change. If subsensors are functionalized for different biological materials, then the electrical properties of each subsensor will change differently depending on the concentration in the measured solution of the particular material they are functionalized for.

One mechanism for which the sensor can work is if the nanowires or nano/micro texture are part of a solar cell, for example on the sunny side of a silicon cell. When light is incident onto a silicon solar cell, the light is absorbed in the silicon nanotexture and creates electron hole pairs. Photocurrent is produced if the electron hole pairs are extracted through the electrical contacts (with one charge having to diffuse across the p-n junction). Photocurrent is not produced if the electron and hole recombine before being extracted out of the contacts.

An unpassivated or weakly passivated surface serves as a very effective recombination site for photocarriers. Since the surface of the solar cell represents a disruption of the crystal lattice, the surfaces of the solar cell are sites of particularly high recombination. The high recombination rate in the vicinity of a surface depletes this region of minority carriers.

One measurement of the recombination rate at a surface is the surface recombination velocity. In a surface with no recombination, the movement of carriers toward the surface is zero, and hence the surface recombination velocity is zero. In a surface with infinitely fast recombination, the movement of carriers toward this surface is limited by the maximum velocity they can attain.

There are different ways to increase the passivation of a silicon surface. One way is by putting charged particles near the surface. These charges repel like charges and can alter the passivation of the semiconductor surface. Proteins and biomarkers often have a negative charge and thus their presence at an unpassivated or weakly passivated silicon surface can alter the surface passivation. Accordingly, the quality of surface passivation affects the performance the solar cell. Furthermore, the magnitude of the change in the passivation of the silicon surface can be used to deduce the number of analytes present Thus, by shining a light that is absorbed in the nanowire array (or texture) and sensing the change in the electrical signal with illumination (ex. photocurrent), one can determine the concentration of an analyte attached to the silicon surface. In some embodiments, if no analytes are attached, the test chip will be weakly passivated and there will be a minimal optical response. Otherwise, the test chip will be well passivated and the photo-created carriers will be collected from the test chip leading to a strong optical response.

Analytes can be biomarkers, protein, DNA, or any material that one can make to selectively attach to a functionalized silicon surface.

The device design can also be used with planar silicon or microtextured silicon, but nanowires/nanotexture can be especially dependent on the quality of surface passivation since they have a high surface area. For example, the surface area of a nanowire array may be over a hundred or a thousand times greater than that of a flat surface or a single nanowire device. As a result of the high surface to volume ratio, nanotextured or nanowire surfaces can be used in a biosensor and result detection of analytes with a lower level of concentration. The lower threshold of detection can be as low as 10 ng/ml, 1 pg/ml, or even in some cases 1 fg/ml. According to various examples, the biosensor may utilize the sensitivity of electrical properties of the nanowire array, in particular, the quality of the front surface passivation, by measuring the solar cell response in a wavelength range that is sensitive to the front surface, for example light with wavelengths between 350 and 700 nm. If the back surface (non-illuminated side) is being used to attach the analytes, then one may choose to use wavelengths that penetrate deeper into the silicon such as those wavelengths between 700 nm and 1100 nm.

Figure 3:
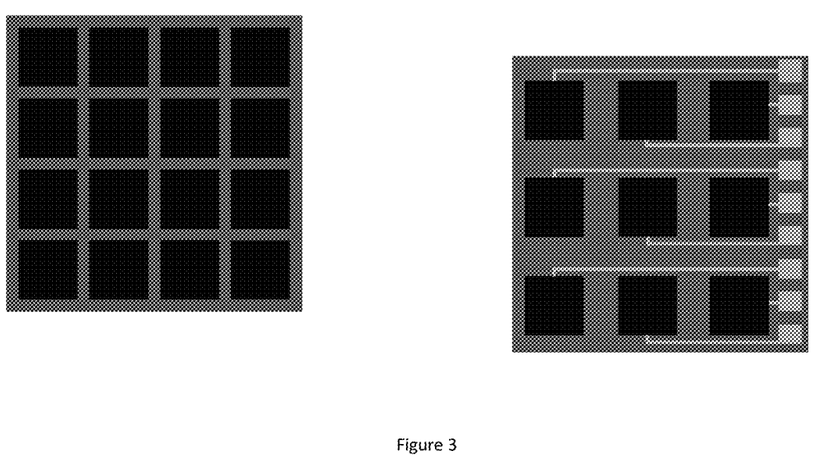
FIG. 3: an example of subsensors and how they can be electrically contacted individually.

The sensor can be subdivided into subsensors with each subsensor, for example, having a thousand to millions of nanowires. Each subsensor may be functionalized to detect a given analyte (e.g., a cancer biomarker, host cell protein, or mutated DNA). One way to implement this invention is to have different antibodies on each subsensor. Thus, with one test, the concentration of many different biological materials in a solution can be measured. There can be for example 10, 20 or 100 different subsensors on the same sensor, each with a different electrical connection. These subarrays can be electrically isolated using, for example, different techniques to create electrical isolation on a silicon chip (e.g., processes used during microelectronic device fabrication). For example, silicon dioxide trenches can be made to create electrically isolated sections within the associated test chip. These sections of the array can be electrically addressed individually, similar to an array used for memory or displays. An example of subsensors and how they can be electrically contacted individually is shown in FIG. 3. In this way, multiple analytes can be detected using the same test chip.

The incident light can either be scanned over a desired section of the nanowire array, or "flashed" to illuminate the entire sample. Once illuminated, the current-voltage of each subarray is taken individually, and a measurement for each subarray group is provided. The light can be incident onto the sample from either the front side, or from both sides and different wavelengths can be used to help better understand the results, where the front refers to the side upon which the light is incident. The nanowires/nanotexture can be on either the front of the back side of the wafer.

The silicon biosensor can either consist of an n-type wafer doped with a p+ region or a p-type wafer doped with an n+ region. The emitter (heavily doped region) can be on either the front or back of the device. The emitter can also be local for example as in either a selective emitter (locally doped under contacts) or interdigitated back contact design (where the two contacts are on the same side of the device). In some cases, one might also choose to use a metal-silicon junction, in which case a heavily doped region may not be needed at all. A tunnel junction may also be desired where the junction forms from tunneling through a dielectric such as silicon dioxide. The tunneling can happen between a metal and silicon through silica.

In some cases, the lightly doped region of the device and/or the p-type region of the device will need to be not covered with metal so that this region of the silicon sensor can be functionalized and exposed to the analyte. In the case of a p-type wafer with n+ region, if one wishes to electrically contact the p-type side while also allowing light to be incident on this side of the device, one can pattern the contacts on this side of the cell. The contacts can be in a comb like fashion.

The most common way to electrically contact lightly p-doped silicon substrates in the solar industry is to use a full aluminum metal coating and then do an anneal so that the aluminum diffuses into the silicon and heavily dopes the silicon surface thus making low resistive contacts. While this approach is very effective for devices for which the light will be incident on the non-metal coated side, it is not effective if the light will be incident onto the lightly doped side as the metal will block most of the light. One solution is to use a thinner metal that is partially transparent. Another solution is to use a transparent conducting contact. Another solution is to pattern the aluminum contacts. Since the nanowires are electrically connected through the base of the wires in the bulk silicon, electrically contacting near but not over the nanowires which have been illuminated with light will still allow one to electrically probe the illuminated nanowires.

In some cases the selectivity of the biosensor can be increased by using the density of the nanowire array as a knob to select which analytes are present. In this case both the antibody as well as the nanowire density can be used to determine which analytes are attached to the surface. More densely packed nanowire arrays may block larger biological molecules from attaching to the surface. The nanowire density can be varied by a variety of techniques such as changing the thickness of the metal used in the metal enhanced etching, changing the concentration of the acid used in the nanowire etch, or by using a mask such as polystyrene to pattern the nanowire array. Furthermore, the space between the nanowires can be increased without decreasing the nanowire density by decreasing the nanowire diameter. This can be done in multiple different ways such as oxidizing and etching the nanowires post processing, It may be benefatable to have very short nanowires or a nanotexture.

In the case of a sensor being divided into subsensors, it might be beneficial to have multiple areas on the sensor in different locations sensitized with the same antibody (or other selective agents like an aptamer). This would allow for verification and checking of results within the same sample and may result in lower false positive results. This technique may also be useful in initial testing where all (or nearly all) of the subsensors can be sensitized with the same antibody.

This can help one to understand better issues of homogeneity of the samples and also any possible inhomogeneity on the chips themselves.

One may also choose to leave unfunctionalized control subsensors on the same chip. This can be done in a pattern such as a "checkerboard" with half the spaces unfunctionalized controls and half functionalized with the same or unique antibodies.

In some cases, more than one protein can bind to a specific antibody. In order to separate out the signals from these multiple proteins, a second test can be used that is selective to only one of the proteins. By using an antibody that is exclusive to a type of protein that also binds to an antibody of another protein of interest, the two tests in combination can be used to deduce the concentrations of each protein individually. So, if protein A is the protein of interest. Antibody A measures both protein A and protein B. Antibody B is selective to protein B and not A. A protein attached to antibody A and not antibody B indicates the presence of protein A. While a protein attached to antibody A and B indicates the presence of protein B. This can help eliminate false positives. The technique of combining tests and creating an algorithm to determine the concentration of particular analytes can be used in general when more than one analyte is measured at a time for some subsensors.

When using the sensor to measure for analytes, one can use a lab setup to illuminate the sample with light and measure the current vs. voltage. However, in manufacturing it is more convenient and easier to use if there is a tool that integrates the illumination and current measurements and then sends this information to a computer. In some cases, tracking the concentrations of proteins as a function of time is important, so the computer can keep track of the measurement results and the time of the measurement and plot the various measurements as a function of time.

To save costs on the measurement system, instead of using a white light source and a spectrometer to select the specific wavelength of light, the system can make use of LEDs or even simple bulbs to shine light on the sample.

The system can be a bench top system where the sensor is placed into a testing chamber. Then the user can select measurements from the computer. The system automatically measures each of the sub-sensors, sends the information to the computer, and presents it in a format that is simple for the user to determine the meaning of the results.

In addition to a tool that can easily measure analyte concentrations using the described sensors, a tool might also be valuable to functionalize the sensors. The described sensor technology is a platform technology that could be useful for many applications. For example, the sensors can be used to measure host cell proteins (unwanted proteins) in biomanufacturing processing, biomarkers for cancer in patient fluids (blood, saliva, . . . ), or growth factors during tissue growth. In each of these examples, the analyte is very different, but the sensor design is the same or almost the same.

Thus, one can design a standard sensor with a set number of subsensors, electrical contacts to each subsensor, and electrical isolation between each subsensor. The only difference between making the sensors for different applications could be just a different functionalization process. Hence, one could make the nanowire sensors up to the point of functionalization. Then once an order for sensors are placed, the sensors can then be functionalized. Alternatively, premade nanowire sensors can be kept in storage until the user decides which proteins to functionalize the sensor for detection of.

In some business models, the time required to fulfill a custom order for a specific sensor needs to be kept short. Manual functionalization of each subsensor is laborious and takes too long. A tool to automatically functionalize the sensors with the desired antibodies could greatly improve the speed and reproducibility of this process.

Figure 4:
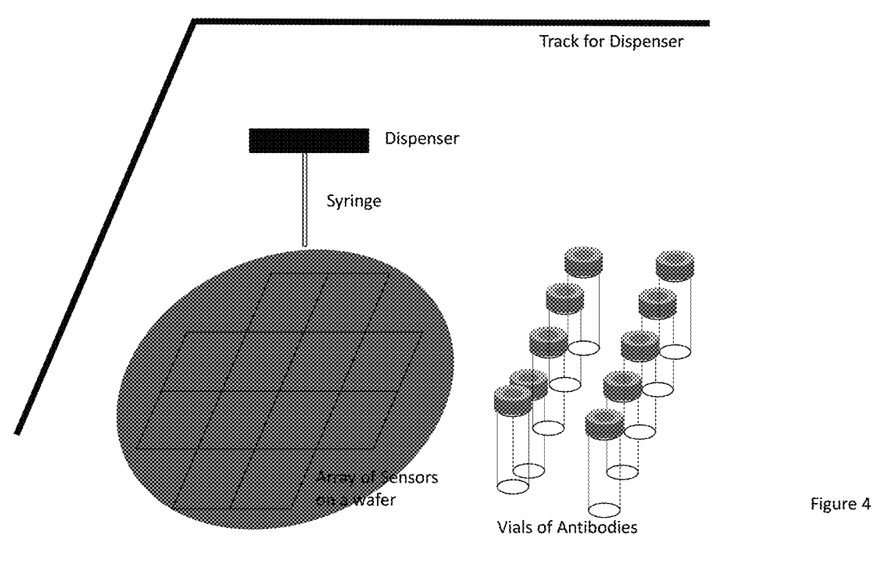
FIG. 4: a tool to automatically functionalize the sensors with the desired antibodies
Figure 5:
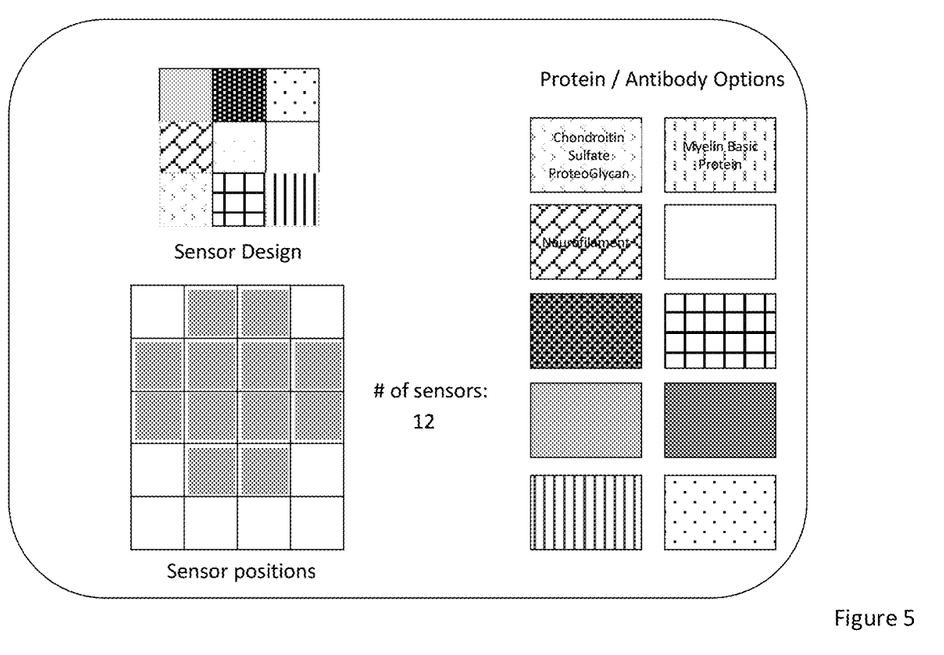
FIG. 5: an example user interface to tell the printer which antibodies to print, in which locations, and how many of this sensor design to make.

In FIG. 4 an example of such a tool is drawn. The sensors are loaded into a holding cell. Then using a pick and place tool, individual sensors are placed into the print chamber. The user, through the user interface (see an example in FIG. 5), tells the printer which antibodies to print, in which locations, and how many of this sensor design to make. The computer and printer then work together to print the desired number of sensors and stores them in an unloading cartridge as they are finished. One such printer could be an ink jet printer.

Exemplary Process

In one example of building a silicon nanowire biosensor we start with a silicon 2-inch wafer, single sided polished, doped with boron, 3 ohm-cm.

Wafer Clean: We clean the wafers by submersing them for 2 min in 10% hydrofluoric acid (HF), doing a triple DI water rinse, then cleaning them in piranha (250 ml of sulfuric acid H2SO4 and 50 ml peroxide $H_2O_2$) for 5 minutes, and then triple rinsing them in DI water a second time.

Nanowire formation: The nanowires can be formed by sputtering a thin layer of silver onto the cleaned wafer. In our case, we often sputter for 20 seconds at 100 W in the sputtering tool.

We then etch the nanowires. This is done by placing the metal coated silicon into 10% HF and bubbling oxygen through the HF solution. We often use an oxygen flow rate of around 12-15 SCCM and etch for around 20 minutes. The wafers are then rinsed three times in DI water.

The metal is then etched off using another piranha solution as described in the wafer cleaning description. The nanowire wafers are then rinsed 3 times in DI water.

Doping preparation: Prior to doping, we coat the side that we don't want to dope with a thick oxide. We often use a plasma enhanced chemical vapor deposition (PECVD) tool to deposit around 10 μm of oxide on the side that we don't want to dope. In our tool this corresponds to 14 min 20 sec, at 300 C, using an RF power of 20 W, 170 SCCM of Silate, 710 SCCM of $N_2O$. We get a rate of about 11.6 A/s. We then do an IPA and acetone clean on a sacrificial wafer and spin coat a spin on phosphorous doping onto this wafer. A spin rate we find works well is 100 RPM.

Doping: We begin the doping process by annealing the sacrificial wafer on a hot plate for 10 minutes at 250 C. Next, we make a stack in our furnace with our wafers. We use a scrap wafer, the sacrificial wafer (with the doping face up), and the nanowire wafer (oxide side up so that the side you want to dope is nearest to the sacrificial wafer). We heat up the furnace to around 1000 C (900-1100 C) and keep it there for around 60 minutes (0 minutes to several hours). We then turn off the furnace and let it cool before removing the wafers.

Contacts: The next step is to put contacts onto the sensor. We first remove the oxide by doing a 10+ minute HF etch, leaving it in the etch until the oxide is removed as noted by the dewetting of the surface. We then deposit aluminum on the p doped region. We often use a comb structure to allow light onto the sample while providing a low resistive path for carriers. The aluminum can be deposited by sputtering, evaporation, or screen printing; the latter two works better with masks. We deposit about 2000 A of Al in the evaporator. No matter how the metal was deposited, an anneal is needed to diffuse the Al into the silicon and make a p+ region under the Al. This will lead to higher quality contacts. We often use an 835 C 4 second rapid thermal anneal (RTA) for this purpose. In some sensors we deposit silver to contact the n-type region. Silver can be deposited by screen printing, sputtering, or evaporation and can be done through a mask to form the desired contact structure. We sometimes evaporate about 500 A of silver and do an RTA for 2 seconds at 735 C Scribe: The sensors can then be scribed or cleaved or cut or sawn from the wafer. Scribe serves the purpose of providing junction isolation as well as separating the devices.

Functionalize the sensor: In order to attach an antibody to the silicon surface, we first prepare 3-(aminopropyl) triethoxysilane (APTES)/ethanol (EtOH) solution. 1% v:v APTES in a premade 95% EtOH/5% H2O solution. We allow the solution to sit for 20 min and then filter it with a 0.2 µm syringe filter. We then place the sensor into the APTES/EtOH solution for 30 min. Then we wash the sensor in EtOH for 50 seconds. Next, we place the chip in an anti-protein solution. In this example, we used an anti-*E. Coli* HCP solution with 10-100 µg/ml anti-*E. Coli* host cell protein (HCP) in 10 mM phosphate buffer solution (PBS) containing (some concentration 1 mM) EDC and (some concentration 2.5 mM) NHS. We allow the solution to react with the sensor for 2-3 hours at room temperature. The sample is now functionalized to be sensitive to *E. Coli* HCP.

Measure: We then measure the current-voltage response of the sensor both with and without light. We measure both through the p and the n sides of the wafer as these tell us different information about the sensor.

Expose to protein: In one example of this invention, we dilute the HCP in phosphate buffer solution to the desired concentration, for example 10 mg/mL and expose the sample for a set time in the protein. Other buffer solutions with different dielectric functions can be used as well. Times can vary between minutes and a few hours. We then remeasure the samples as before and compare the photocurrent to before and after the protein exposure to measure protein concentration.

Accordingly, the disclosed aspects and embodiments have an enormous potential across various applications as a result of the ultra-sensitivity, selectivity, ability to measure the number of analytes quantitatively, the lack of labels, and real-time detection capabilities discussed herein.

All patents, patent applications, and publications mentioned in this application are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The following references may be relevant to this application: (1) Sami Franssila, *Introduction to Microfabrication* (2d ed. John Wiley Et Sons 2010). (2) U.S. Published Patent Application No. 2009/256134. (3) U.S. Pat. No. 8,852,981. (4) H. Galinski et al., "Agglomeration of Pt thin films on dielectric substrates," *Phys. Rev. B*, 82, 235415 (2010). (5) Feng-Ming Liu Et Mino Green, "Efficient SERS substrates made by electroless silver deposition into patterned silicon structures," *J. Mater. Chem.*, 14, 1526-1532 (2004). (6) D. W. Pashley et al., "The growth and structure of gold and silver deposits formed by evaporation inside an electron microscope," *Phil. Mag.*, 10:103, 127-158 (1964). (7) Muller, Richard S., Theodore I. Kamins, Mansun Chan, and Ping K. Ko. "Device electronics for integrated circuits." (1986): 54. (8) Weste, Neil H E, and Kamran Eshraghian. "Principles of VLSI Design." A Systems Perspective 2 (1985). (9) U.S. Pat. No. 8,450,599. (10) U.S. Pat. No. 8,143,143. (11) U.S. Pat. No. 10,079,322.

All patents, patent applications, and publications mentioned in this application are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

Applications As discussed herein, in various aspects and embodiments the biosensor may include an array of nanowires which are configured to measure indications of cancer, and other illnesses. Such aspects and embodiments offer the benefits of earlier cancer detection, and less medical waste (e.g., smaller blood samples). Applications also include measuring host cell proteins or other proteins in biomanufacturing. The sensors could also be used to monitor a person's health outside a doctor's office. Or example, one can measure biomarkers, proteins, or DNA in urine, spit, bowel movements, or from a pin prick and drop of blood.

Sensors can be used to measure biomarkers on a regular basis and recorded as a function of time to allow the person to track changes in biomarkers. The measurement tool can be made to communicate with a computer that keeps track of measurements and the time of measurements. This connection can be wireless or wired. The measurement tool can be placed on the body or in locations such as the toilet for easy access to bodily fluids.

Tests can be used to indicate diseases, measure protein in the urine for diabetes for example, indicate times of fertility, or optimize for high performance sports training.

The term "nanostructure" as used herein, refers to a structure typically characterized by at least one physical dimension less than about 300 nm. In this nanostructure a property of interest is different that that of bulk, or not nanostructured materials.

The term "nanowire" describes a material with a shape that typically has one principle axis that is longer than another dimension which is nanostructured. Thus, they have an aspect ratio greater than one and often greater than 2 or 5. In certain embodiments, nanowires herein have a substantially uniform diameter. In some embodiments, the diameter shows a variance along the axis of the wire. In some embodiments, the wires have a roughly circular cross section, but in other embodiments, the cross section is oval or other non-circular shapes.

It will be appreciated that the term "nanostructure" can include structures such as nanopyramids, nanowires, nanotubes, nanopores, and other nanosized features.

The term "functionalized" refers to the process of attaching one or more functional moiety (antibody, antigen, ligand, etc.) such as a chemically reactive group to the surface. The nano-surface us functionalized to for example confer specificity for a desired analyte in a reaction such as in an assay. Those skilled In the art will be aware of many different functionalization methods which can be used.

The invention claimed is:

1. A sensor device comprising:
   a bulk region with an upper surface and a lower surface;
   nanowires in an aligned array or a nanowire array which contact the upper surface of the bulk region, wherein all nanowires in the array have one predominant type of dopant, n or p, and at least a portion of the bulk region also comprises that predominant type of dopant and the rest of the bulk region has the other type of dopant, wherein the upper surface of the bulk region lies substantially along a plane and the nanowires are aligned normal to that plane and a heaviest doped region is not in the nanowire array, but in the bulk region on the upper side of the device, the sensor device being functionalized to be have modified electrical properties when proteins are present; and
   at least two electrical contacts.

2. The sensor device of claim 1, wherein the bulk region and the nanowires are made of silicon.

3. The sensor device of claim 1, wherein a junction between the n and the p regions occur on the side of the bulk region opposite to that of the nanowire array.

4. The sensor device of claim 1, wherein the nanowires are p-type doped and a back-side of the bulk region is more heavily n-type doped.

5. The sensor device of claim 4, wherein the nanowires are doped to a level of $10^{17}/cm^3$, $10^{16}/cm^3$, or $10^{15}/cm^3$.

6. The sensor device of claim 1, wherein the nanowires are n-type doped and the back-side of the bulk region is more heavily p-type doped.

7. The sensor device of claim 6, wherein the nanowires are doped to a level of $10^{17}/cm^3$, $10^{16}/cm^3$, or $10^{15}/cm^3$.

8. The sensor device of claim 1 wherein the device is functionalized with antibodies that selectively attach a protein of interest.

9. The sensor device of claim 8, wherein the proteins of interest are host cell proteins.

10. The sensor of device of claim 8, wherein subsections are created on the sensor which are functionalized to detect different proteins of interest.

11. The sensor of device of claim 9, wherein different subsections are functionalized to detect different host cell proteins.

12. The sensor device of claim 1, wherein one of the at least two electrical contacts includes a selective emitter disposed on the upper surface of the bulk region.

* * * * *